United States Patent [19]

Palmer

[11] Patent Number: 5,330,775
[45] Date of Patent: Jul. 19, 1994

[54] STERILITY CONTROL OF FOOD PRODUCT BY INTRODUCING A HARMLESS NON-STERILE COMPONENT

[75] Inventor: Roland A. Palmer, Eversley, England

[73] Assignee: The New Covent Garden Soup Company Limited, London, United Kingdom

[21] Appl. No.: 613,569

[22] PCT Filed: Oct. 3, 1988

[86] PCT No.: PCT/GB88/00815
§ 371 Date: Nov. 27, 1990
§ 102(e) Date: Nov. 27, 1990

[87] PCT Pub. No.: WO89/02928
PCT Pub. Date: Apr. 6, 1989

[30] Foreign Application Priority Data

Oct. 2, 1987 [GB] United Kingdom ............... 8723139

[51] Int. Cl.$^5$ ................................................ A23L 1/39
[52] U.S. Cl. ...................................... 426/61; 426/589; 426/43; 426/56; 426/52; 426/87
[58] Field of Search ................ 426/43, 52, 56, 61, 426/589, 383, 232, 87, 61

[56] References Cited

U.S. PATENT DOCUMENTS

| | | |
|---|---|---|
| 2,485,566 | 10/1949 | Clark . |
| 3,206,317 | 9/1965 | Golber . |
| 3,899,594 | 8/1975 | Nickerson et al. . |
| 4,874,704 | 10/1989 | Boudreaux et al. ............... 426/61 |
| 4,894,243 | 1/1990 | Ahrné ............................... 426/43 |

FOREIGN PATENT DOCUMENTS

| | | |
|---|---|---|
| 78112 | 5/1983 | European Pat. Off. . |
| 92183 | 10/1983 | European Pat. Off. . |
| 1530476 | 11/1978 | United Kingdom . |
| 1549196 | 7/1979 | United Kingdom . |
| 1579926 | 11/1980 | United Kingdom . |

OTHER PUBLICATIONS

Froud, N., 1972, "The World Book of Soups", Drake Publishers Inc., New York, pp. 97 & 108.
DeGouy, L. P., 1949, "The Soup Book—770 Recipes", Dover Publications Inc., New York, pp. 162-163.
Berolzheimer, R., 1953, "250 Delicious Soups", Consolidated Book Publishers, Chicago, Ill., p. 17.
Montagne, P. 1977, "The New Laronsse Gastronomique", Crown Publishers, Inc. New York, pp. 816-819.

Primary Examiner—Joseph Golian
Attorney, Agent, or Firm—Sandler Greenblum & Bernstein

[57] ABSTRACT

A liquid food product, such as a soup or sauce, is treated by first sterilizing it, e.g. by UHT processing, and then introducing into it a minor amount, e.g. 5 to 15 vol. %, of a non-sterile component, e.g. a dairy product, substantially free of all micro-organisms liable to cause disease. The non-sterile component will cause evident harmless spoilage of the product after a given period of storage, so that the consumer will be obliged to discard the product before any harmful bacteria have grown.

10 Claims, No Drawings

STERILITY CONTROL OF FOOD PRODUCT BY INTRODUCING A HARMLESS NON-STERILE COMPONENT

This invention relates to liquid food products such as soups and sauces, and to methods of treating such products so as to extend their permissible shelf life.

Soups, sauces, and other liquid food products of low acidity (pH>4.5) can provide an ideal environment for the growth of micro-organisms. They are generally made from a wide variety of ingredients and can carry a wide range of initial micro-organisms. Treatment at high temperature under pressure (UHT processing) substantially sterilizes the product, but micro-organisms remaining in minute amounts or entering the packaging can produce the risk of food poisoning or other diseases. Consequently, if the packaging is not aseptic the permitted shelf life must be short (of the order of days). Aseptic packaging increases the cost of the product to the consumer.

The present invention is based on the idea of introducing into a sterilized liquid food product a known micro-biological contaminant which will cause evident spoilage of the product after a given period of storage, so that the consumer will be obliged to discard the product before any harmful bacteria have grown.

The invention provides a liquid food product comprising a major component which is substantially sterile and a minor component which is non-sterile but substantially free of all micro-organisms liable to cause disease.

The invention also provides a method of treating a liquid food product, comprising sterilizing the food product and then introducing into it a minor amount of a non-sterile component substantially free of all micro-organisms liable to cause disease.

The preferred sterilization procedure is heating above 100° C. at superatmospheric pressure, but any other convenient procedure may be used, e.g. irradiation.

The non-sterile component may be any suitable medium carrying one or more types of food spoilage micro-organism, in such a quantity that after mixing with the sterile component there are sufficient food spoilage organisms to substantially ensure that, after packing, preferably in a hermetically sealed container, there will be at least one spoilage organism per pack. The number of spoilage organisms required in each batch of the food product will depend on the pack size: the larger the pack size, the lower the number of organisms required. It is preferable for the non-sterile component to be a natural food substance, of animal or vegetable origin, produced under conditions in which it is free of disease-causing micro-organisms but will inevitably contain food-spoiling bacteria. Such substances, e.g. raw or pasteurised dairy products, are cheap and readily available, and they may enhance the flavour of the product.

Since the food spoilage eventually caused by the non-sterile component will be evident to the consumer, it will prevent him from consuming the food product after the nominal permitted storage period has elapsed. In the absence of such evident spoilage, a food product might be kept for too long and become contaminated with harmful, not readily detectable bacteria. Suitable evidence of spoilage may be a change in texture (thickening), appearance (colour), and/or smell.

EXAMPLE

Production of Fresh Soups and Sauces

After prior preparation, the ingredients of the soup or sauce are mixed in an agitated processing vessel and are subjected to a short period of processing at high temperature under pressure. The time and the temperature depend on the ingredient mixture and the size of any particulates in the liquid phase.

The product is then rapidly cooled by vacuum to 100° C., when a predetermined quantity of raw or pasteurised dairy products are added to the batch by vacuum (5 to 15% by volume).

The temperature of the batch is then stabilised at 75°–85° C. and the product is fed via sterile pipework and filled into clean containers ensuring that the temperature after filling is in excess of 75° C. (pasteurisation temperature).

The containers are immediately sealed and held for two minutes to ensure pasteurisation of the container. They are then rapidly cooled to refrigerated storage temperatures and are ready for distribution under refrigerated conditions.

No artificial food additives or stabilisers are used in the final product or as processing aids.

The process is applicable to a wide range of low acid liquid foods where:

the initial ingredients may carry varied and non-specific microbiological load;

dairy products which have not been subjected to UHT processing (e.g. raw milk and cream, pasteurised milk, skimmed milk, or cream) are usable as one of the ingredients;

the packaging system is clean but not aseptic. The containers used may be gabletopped cartons manufactured under the trade mark "Purpak".

The use of high temperature short time cooking effectively kills the initial loading of bacteria and renders the product commercially sterile and the product can be considered free of micro organisms.

The addition of the dairy products (described above) at the stage described above acts as a microbiological flag. While the heat treatment of the dairy products will kill all vegetative organisms, certain heat resistant spores which are invariably present in pasteurised milk will survive (mainly of the Bacillus group).

These spores have known and predictable growth patterns and will serve to spoil the product after given periods at differing temperatures. They will cause obvious signs of food spoilage and serve to warn consumers that the product is potentially unsafe. During the process a sufficient quantity of dairy product is added to ensure that there is not less than one spoilage organism per pack.

The process ensures that after packing the product has a very low initial microbe count and that therefore under optimal storage conditions will have an extended life, but at the same time it ensures that certain naturally occurring food spoilage organisms are present.

The spores in dairy products after pasteurisation are of a particular type, with known behavioural and growth patterns. They have certain beneficial characteristics which will reduce the risks of food poisoning:

under refrigerated conditions they will grow slowly but will not spoil the product until it has past its commercial shelf life;

they will provide competition for (and therefore reduce the growth rate of) any food poisoning organisms which may contaminate the product as a result of poor process control or post process contamination occurring while the product is in the control of the manufacturer, distributor, or final consumer;

they will grow faster than known food poisoning organisms, thus obvious food spoilage will occur before any food poisoning bacteria has grown sufficiently to produce dangerous levels of toxins; they will grow quickly if the product is not refrigerated or is otherwise abused, and will cause obvious food spoilage.

I claim:

1. In a method for treating and packaging a liquid food product for temporary storage under controlled conditions and distribution to consumers, comprising the steps of sterilizing the food product and then sealing it in a container, the improvement comprising introducing into the food product, after the sterilization step and before the sealing step, a non-sterile component substantially free of all micro-organisms liable to cause disease but containing food-spoilage bacteria for causing evident spoilage of the food product after a given period of storage under controlled conditions.

2. A method as claimed in claim 1, in which the non-sterile component is a natural food substance produced under conditions in which it is free of disease-causing micro-organisms but will inevitably contain food-spoilage bacteria.

3. A method as claimed in claim 2, in which the non-sterile component comprises a dairy product.

4. A method as claimed in claim 2, in which the non-sterile component is pasteurised.

5. A method as claimed in claim 1, in which the sterilization of the food product comprises heating above 100° C. at superatmospheric pressure.

6. A method as claimed in claim 1, in which the non-sterile component makes up 5 to 15% by volume of the resulting product after treatment.

7. A method as claimed in claim 1, in which the food product is a soup or sauce.

8. A method as claimed in claim 1, in which the food product is of low acidity, i.e. pH $>4.5$.

9. A method as claimed in claim 1, in which the introduction of the non-sterile component and the sealing of the container take place at pasteurization temperature.

10. An article of commerce made by the method of claim 1.

* * * * *